United States Patent [19]

Okamoto et al.

[11] Patent Number: 4,945,088

[45] Date of Patent: Jul. 31, 1990

[54] INSECTICIDAL WETTABLE POWDER

[75] Inventors: Yukikazu Okamoto, Ikeda; Manabu Tagami, Nishinomiya; Goro Shinjo, Toyonaka; Kozo Tsuji, Nara, all of Japan

[73] Assignee: Sumitomo Chemical Company, Limited, Osaka, Japan

[21] Appl. No.: 701,456

[22] Filed: Feb. 14, 1985

[30] Foreign Application Priority Data

Sep. 21, 1982 [JP] Japan ................. 57-165442

[51] Int. Cl.$^5$ ............... A01N 57/00; A01N 25/00
[52] U.S. Cl. ..................... 514/132; 514/86; 514/122; 514/770
[58] Field of Search ............ 514/132, 86, 122, 770

[56] References Cited

U.S. PATENT DOCUMENTS

| | | | |
|---|---|---|---|
| 3,227,657 | 1/1966 | Haden | 424/357 |
| 3,232,831 | 2/1966 | Schwint | 424/357 |
| 4,172,146 | 10/1979 | Karrer | 424/308 |
| 4,307,115 | 12/1981 | Klopping . | |

FOREIGN PATENT DOCUMENTS

| | | |
|---|---|---|
| A96015 | of 1974 | Japan . |
| 6669 | 7/1980 | Japan . |
| 1209996 | 10/1970 | United Kingdom . |
| 1346446 | 2/1974 | United Kingdom . |

OTHER PUBLICATIONS

WHO Chronicle, 31 102–105 (1977).
Farm Chemicals Handbook; C213, 1983.
Bull. WHO, 56 (3), 445–452 (1978).
WHO/VBC/76.645 (1976).

*Primary Examiner*—Joseph A. Lipovsky
*Attorney, Agent, or Firm*—Stevens, Davis, Miller & Mosher

[57] ABSTRACT

Insecticidal wettable powders containing an insecticide which is liquid at room temperature and a calcined synthetic hydrated silicon dioxide, which can retain its insecticidal effect for a long time without separating oil drops when used by diluting with water.

3 Claims, No Drawings

INSECTICIDAL WETTABLE POWDER

This application is a continuation-in-part of application Ser. No. 532,479, filed Sept. 15, 1983, now abandoned.

The present invention relates to insecticidal wettable powders containing as an active ingredient an insecticide which is liquid a room temperature (20° to 25° C.) and as a carrier a calcined synthetic hydrated silicon dioxide (hereinafter referred to as calcined white carbon).

Hitherto, when an insecticide which is liquid at room temperature was formulated into a wettable powder, highly oil-absorptive fine solid powders, for example synthetic hydrated silicon dioxide (hereinafter referred to as white carbon), diatomaceous earth, Attapulgite clay, montmorillonite clay and the like have been used as carriers. Particularly, white carbon is widely used because it has a high oil-absorptive capacity and causes little decomposition of most insecticides. Of these wettable powders, for example a fenitrothion wettable powder is widely used in controlling malaria mosquitoes, etc. When this wettable powder is diluted with water into a suspension and sprayed onto the wall surface of houses and the like in order to control insect pests such as mosquitoes, flies, etc., coming into contact with the surface, if the wall surface is not absorptive as e.g., stone, overlayed plywood, etc., an insect pests controlling effect can be maintained over a long period of time. But, if the wall surface is absorptive such as the leaves and bark of woods and grasses, soil walls, concrete walls, etc., it is difficult to maintain the insect pests controlling effect over a long period of time. Further, depending upon the kinds of carrier and dispersing agent added to the formulation, insecticides, when diluted with water into a suspension, sometimes separate from the suspension in the form of oil drops.

The present inventors found that, when calcined white carbon is used as a carrier for the wettable powder of insecticides of liquid state at room temperature, the insecticides, even if diluted with water into a suspension, do not separate in the form of oil drops, and that, when the suspension is sprayed onto absorptive wall surfaces to control insect pests, the insect pests controlling effect can be maintained over a long period of time, and therefore that, in controlling mosquitoes, flies, etc., the number of sprayings and amount of spray volume can be decreased. The present invention was completed based on this finding.

The insecticidal wettable powder of the present invention contains as an active ingredient an insecticide which is liquid at room temperature and as a carrier calcined white carbon. At the time of formulation, however, some kinds of dispersing agents and diluents may be added. As the active ingredient, insecticides which are liquid at room temperature, particularly organophosphorous insecticides having a high effect in controlling insect pests such as mosquitoes, flies, etc., for example fenitrothion, pirimiphos-methyl, malathion, diazinon, etc. are used. In addition to these insecticides, other chemicals, for example tetramethrin, cyphenothrin, permethrin, phenothrin, deltamethrin, kadethrin, cyfluthrin, furethrin, fenvalerate, etc. may be added, but said mixture must maintain a liquid state at room temperature.

Calcined white carbon is obtained by calcining white carbon produced by the wet process (Farm Chemicals Handbook, C213, 1983), for example Tokusil® (Tokuyama Soda Co.), Carplex® (Shionogi Seiyaku Co.), Nipsil® (Nippon Silica Co.), Vitasil® (Taki Chemical Co.) and the like, at 600° to 900° C., preferably 600° to 800° C. But, those which show an alkaline property when diluted with water or have a particle diameter of not less than 10 μ after calcination are not preferred. A dispersing agent may be added, and when it is added, anionic surface active agents such as ligno-sulfonates, alkyl sulfates, alkylaryl sulfonates, etc., dextrin, gum arabic, carboxymethyl cellulose (hereinafter referred to as CMC) and the like are used. But, those which emulsify the insecticides, which are an active ingredient, are not preferred.

A diluent also may be added, and when it is added, fine powders of low oil absorption, for example calcium carbonate, silica powder, talc, grape sugar, cane sugar, ammonium sulfate, ammonium phosphate, urea, etc. are used.

The content of the insecticide which is in the liquid state at room temperature, an active ingredient, in the wettable powder is generally 10% to 75%, preferably 40% to 60%, and the amount of calcined white carbon, a carrier, is one-third of to equal the amount of active ingredient.

The insecticidal wettable powder of the present invention can easily be produced by standard equipment known to those skilled in the art. Referring now to the method, firstly, calcined white carbon and, as need arises, powdery components such as a diluent, finely pulverized dispersing agent, etc. are added to a ribbon mixer or screw mixer. While mixing the mixture at room temperature or, as need arises, at a raised temperature of 30° to 80° C., an active ingredient, i.e. the insecticide of liquid state at room temperature or, if necessary, its liquid mixture with other insecticides, which form a liquid mixture with it, and a dispersing agent, if necessary, is poured into said mixture and mixed therewith. In this case, said active ingredient may be at room temperature or, as need arises, at a raised temperature of 30° to 80° C. Thereafter, in order to obtain a thoroughly uniform mixture of the active ingredient and dispersing agent, the lumps are pulverized by passing the resulting mixture through a pulverizer such as a hammer mill or pin mill. Finally, the resulting mixture is mixed again uniformly in a ribbon mixer or a screw mixer to obtain the objective insecticidal wettable powder.

In the foregoing steps of mixing, pulverizing and mixing, if a high-speed rotating-blade type mixer such as juice mixer or Henschel mixer (Mitsui Miike Seisakusho Co.) is used, every step above can be carried out in the same mixer by mere regulation of stirring rate.

Next, the present invention will be illustrated with reference to the following examples, comparative examples and test examples. All parts and percents in these examples are by weight.

EXAMPLE 1

Commercially available white carbon (Carplex #80) was calcined in an electric furnace at varying temperatures of 600° C., 700° C., 800° C. and 900° C. for 3 hours. Forty parts of each calcined white carbon obtained was weighed into a glass beaker, and 60 parts of fenitrothion was added. After thorough mixing with a glass rod, the mixture was mixed on a high-speed rotating-blade type mixer (juice mixer) for 5 minutes at room temperature. Four kinds of fenitrothion wettable powder were thus obtained.

EXAMPLE 2

Three kinds of commercially available white carbon (Tokusil P, Nipsil N300A and Carplex #80) were each calcined at 700° C. for 1 hour in an electric furnace in the same manner as in Example 1. Sixty parts of fenitrothion was added to 40 parts of each calcined white carbon obtained, and three kinds of fenitrothion wettable powder were then obtained in the same manner as in Example 1.

EXAMPLE 3

Commercially available white carbon (Carplex #80) was calcined at 700° C. for 3 hours in the same manner as in Example 1. Thereafter, 32.5 parts of the calcined white carbon obtained and 3 parts of sodium dodecylbenzenesulfonate were weighed into a ribbon mixer, and while mixing the mixture at room temperature, 64.5 parts of fenitrothion heated to 40° C. was poured into the mixture, followed by mixing for 10 minutes. The resulting mixture was pulverized and mixed by a hammer mill, and then mixed in a ribbon mixer at room temperature for 10 minutes to obtain a fenitrothion wettable powder.

EXAMPLE 4

Commercially available white carbon (Tokusil P) was calcined at 800° C. for 1 hour in the same manner as in Example 1. Using the calcined white carbon obtained, a fenitrothion wettable powder was obtained in the same manner as in Example 3.

EXAMPLE 5

A fenitrothion wettable powder was obtained in the same manner as in Example 3 using 27 parts of the same calcined white carbon as in Example 3, 26 parts of calcium carbonate, 2 parts of calcium lignosulfonate, 2 parts of sodium lauryl sulfate and 43 parts of fenitrothion.

EXAMPLE 6

A fenitrothion wettable powder was obtained in the same manner as in Example 3 using 27 parts of the same calcined white carbon as in Example 4, 27 parts of grape sugar, 3 parts of sodium dodecylbenzenesulfonate and 43 parts of fenitrothion.

EXAMPLE 7

Commercially available white carbon (Nipsil N300A) was calcined at 800° C. for 3 hours in the same manner as in Example 1. A fenitrothion wettable powder was obtained in the same manner as in Example 3 using 22 parts of the calcined white carbon obtained, 1 part of sodium lauryl sulfate, 2 parts of CMC, 53.5 parts of ammonium phosphate and 21.5 parts of fenitrothion.

EXAMPLE 8

Commercially available white carbon (Tokusil GU-N) was calcined at 800° C. for 1 hour in the same manner as in Example 1. A fenitrothion wettable powder was then obtained in the same manner as in Example 3 using 25 parts of the calcined white carbon obtained and 75 parts of fenitrothion.

EXAMPLE 9

A pirimiphos-methyl wettable powder was obtained in the same manner as in Example 6 but using pirimiphos-methyl in place of fenitrothion.

EXAMPLE 10

A malathion wettable powder was obtained in the same manner as in Example 3 using 40 parts of the same calcined white carbon as in Example 4, 3 parts of calcium lignosulfonate, 2 parts of sodium alkylnapthalenesulfonate and 55 parts of malathion.

EXAMPLE 11

A diazinon wettable powder was obtained in the same manner as in Example 5 but using diazinon in place of fenitrothion.

EXAMPLE 12

A fenitrothion.tetramethrin wettable powder was obtained in the same manner as in Example 3 using 27 parts of the same calcined white carbon as in Example 3, 23.9 parts of calcium carbonate, 2 parts of calcium lignosulfonate, 2 parts of sodium lauryl sulfate, 43 parts of fenitrothion and 2.1 parts of tetramethrin.

EXAMPLE 13

Commercially available white carbon (Nipsil N300A) was calcined at 800° C. for 3 hours in the same manner as in Example 1. A fenitrothion wettable powder was obtained in the same manner as in Example 3, using 10 parts of the calcined white carbon obtained, 1 part of sodium lauryl sulfate, 2 parts of CMC, 77 parts of ammonium phosphate and 10 parts of fenitrothion.

COMPARATIVE EXAMPLE 1

To 40 parts each of the same commercially available white carbon (Carplex #80), as non-calcined, as in Example 1 and the calcined products of the same white carbon obtained by 3 hours' calcination at varying temperatures of 300° C., 500° C. and 1000° C., was added 60 parts of fenitrothion. Four kinds of fenitrothion wettable powder were then obtained in the same manner as in Example 1.

COMPARATIVE EXAMPLE 2

Three kinds of fenitrothion wettable powder were similarly obtained using the same white carbon as in Example 2 as non-calcined.

COMPARATIVE EXAMPLES 3, 4, 5 and 6

Fenitrothion wettable powders were obtained in the same manner as in Examples 3, 4, 5 and 6 except that the calcined white carbon in each Example was replaced by the non-calcined white carbon.

COMPARATIVE EXAMPLES 7, 8 and 9

A pirimiphos-methyl, malathion and diazinon wettable powders were obtained in the same manner as in Examples 9, 10 and 11, respectively, except that the calcined white carbon in each Example was replaced by the non-calcined white carbon.

TEST EXAMPLE 1

Ten grams each of the fenitrothion wettable powders obtained in Example 1 and Comparative Example 1 was added to a 200-ml beaker containing 90 ml of water having a hardness of 19.2 degrees. The mixture was slowly stirred with a glass rod, and separated oil drops at the bottom of the beaker were sucked up with an absorbing tube. The amount of the separated oil was then measured. The result is shown in Table 1.

TABLE 1

| Calcination temperature (°C.) | Physical properties of calcined synthetic hydrated silicon dioxide | | | Amount of separated oil drops (ml) |
|---|---|---|---|---|
| | Water content (%) | Oil absorption (%) | Specific surface area (m²/g) | |
| Not calcined | 6.0 | 240 | 188 | 2 |
| 300 | 6.7 | 260 | 169 | 2 |
| 500 | 4.1 | 270 | 153 | 1.5 |
| 600 | 2.3 | 270 | 145 | <0.1 |
| 700 | 1.8 | 280 | 136 | 0 |
| 800 | 0.7 | 250 | 122 | 0 |
| 900 | 0.6 | 220 | 89 | <0.1 |
| 1000 | 0.1 | 60 | 5 | 5 |

The physical properties of the calcined synthetic hydrated silicon dioxide were measured by the following methods.

Water content: Calcined synthetic hydrated silicon dioxide was allowed to absorb moisture to a constant weight by allowing it to stand at a humidity of 50 to 60% and a temperature of 20° to 25° C. The silicon dioxide was then heated at 105° C. to obtain a loss in weight by drying from which the water content (%) was calculated.

Oil absorption: The oil absorption of fenitrothion was obtained according to the testing method for oil absorption with linseed oil described in JIS K 5101 (Testing method for pigments).

Specific surface area: Obtained by the BET-$N_2$ adsorption method (MONOSOLV, Yuasa Battery Co.)

TEST EXAMPLE 2

In the same manner as in Test Example 1, the fenitrothion wettable powders each obtained in Example 2 and Comparative Example 2 was added to hard water of 19.2 degrees, and the amount of separated oil drops was measured.

The result is shown in Table 2.

TABLE 2

| Kind of synthetic hydrated silicon dioxide | Physical properties of synthetic hydrated silicon dioxide | | | Amount of separated oil drops (ml) |
|---|---|---|---|---|
| | Water content (%) | Oil absorption (%) | Specific surface area (m²/g) | |
| Calcined product of Tokusil P | 1.4 | 270 | 144 | 0 |
| Calcined product of Nipsil N300A | 1.5 | 270 | 145 | 0 |
| Calcined product of Carplex #80 | 1.6 | 280 | 133 | 0 |
| Tokusil P | — | 270 | 180 | 2 |
| Nipsil N300A | — | 270 | 163 | 2 |
| Carplex #80 | — | 240 | 188 | 2 |

The physical properties of the synthetic hydrated silicon dioxide were measured in the same manner as in Test Example 1.

TEST EXAMPLE 3

Using the fenitrothion wettable powders obtained in Examples 3, 4, 5 and 6 and Comparative Example 3, 4, 5 and 6, the amount of separated oil drops was obtained in the same manner as in Test Example 1. Further, the insect pests controlling effect on mud brick, which is an absorptive wall surface, was examined.

The result is shown in Table 3.

TABLE 3

| Test wettable powder | Amount of separated oil drops (ml) | Mortality of common mosquito (%) | | | | |
|---|---|---|---|---|---|---|
| | | After 2 hours | After 1 week | After 2 weeks | After 4 weeks | After 8 weeks |
| Wettable powder obtained | | | | | | |
| in Example 3 | 0 | 100 | 100 | 100 | 100 | 98 |
| in Example 4 | 0 | 100 | 100 | 100 | 100 | 100 |
| in Example 5 | 0 | 100 | 100 | 99 | 97 | 98 |
| in Example 6 | 0 | 100 | 100 | 100 | 100 | 100 |
| in Comparative Example 3 | 3 | 100 | 83 | 77 | 50 | 37 |
| in Comparative Example 4 | 3 | 100 | 91 | 85 | 64 | 43 |
| in Comparative Example 5 | 2 | 100 | 74 | 67 | 48 | 27 |
| in Comparative Example 6 | 2 | 100 | 90 | 83 | 82 | 55 |

The mortality (%) of common mosquito (*Culex pipiens pallens*) was obtained by the following testing method.

Chemicals-treated mud brick, 20 cm×20 cm in size, was prepared by spraying an aqueous dilute suspension of test wettable powder onto the brick so that the amount of fenitrothion as active ingredient was 2 g/m², by means of a spray gun at a place 30 cm apart from the brick.

This mud brick was stored at a temperature of 25° C.±2° C. and the humidity of 60%±10%, and applied to the following test after 2 hours, one week, 2 weeks, 4 weeks or 8 weeks.

A plastic cage, 9 cm in diameter and 1 cm in depth, was placed on the chemicals-treated mud brick, and 20 female adults of common mosquito were liberated therein. After one hour, the female adults were transferred into a clean plastic cup with 5% sugar aqueous solution. After 24 hours, the number of killed adults was counted, and the mortality was calculated from it.

As apparent from the test results, the fenitrothion wettable powder of the present invention retains its insect pests controlling effect for a long period of time on the absorptive surface.

TEST EXAMPLE 4

Using the pirimiphos-methyl wettable powders obtained in Example 9 and Comparative Example 7, the malathion wettable powders obtained in Example 10 and Comparative Example 8 and diazinon wettable powders obtained in Example 11 and Comparative Example 9, the insect pests controlling effect on mud brick was examined in the same manner as in Test Example 3. the result is shown in Table 4.

TABLE 4

| Test wettable powder | Mortality of common mosquito (%) | | | |
| --- | --- | --- | --- | --- |
| | After 2 hours | After 2 weeks | After 4 weeks | After 8 weeks |
| Wettable powder obtained | | | | |
| in Example 9 | 100 | 100 | 100 | 100 |
| in Comparative Example 7 | 100 | 100 | 43 | 0 |
| in Example 10 | 100 | 100 | 100 | 98 |

TABLE 4-continued

| Test wettable powder | Mortality of common mosquito (%) | | | |
| --- | --- | --- | --- | --- |
| | After 2 hours | After 2 weeks | After 4 weeks | After 8 weeks |
| in Comparative Example 8 | 100 | 74 | 24 | 0 |
| in Example 11 | 100 | 100 | 100 | 100 |
| in Comparative Example 9 | 100 | 84 | 43 | 14 |

What is claimed is:

1. An insecticidal wettable powder comprising from 10 to 75% of an organo-phosphorous insecticide selected from the group consisting of fenitrothion, pirimiphos-methyl, malathion and diazinon, which is liquid at room temperature, and calcined synthetic hydrated silicon dioxide, wherein the calcined synthetic hydrated silicon dioxide is obtained by calcining a synthetic hydrated silicon dioxide at a temperature of 600° to 800° C. and is present in an amount of one-third of to equal the amount of the insecticide, said liquid organo-phosphorous insecticide not separating as an oil when the insecticidal wettable powder is mixed with water.

2. The insecticidal wettable powder according to claim 1, wherein the insecticide is fenitrothion.

3. A method for controlling insects which comprises applying the insecticidal wettable powder of claim 1 to the insects.

* * * * *